(12) United States Patent
Kluesener et al.

(10) Patent No.: US 6,506,945 B2
(45) Date of Patent: *Jan. 14, 2003

(54) PROCESS FOR PREPARING ETHER-CAPPED POLY(OXYALKYLATED) ALCOHOL SURFACTANTS

(75) Inventors: Bernard William Kluesener, Harrison, OH (US); Mark Robert Sivik, Mason, OH (US); Glenn Thomas Jordan, IV, Indian Springs, OH (US); Paul William Huber, Jr., Dayton, NJ (US); Philippe Neyraval, Trenton, NJ (US); Christian Priou, West Windsor, NJ (US)

(73) Assignee: The Procter & Gamble Company, Cincinnati, OH (US)

(*) Notice: Subject to any disclaimer, the term of this patent is extended or adjusted under 35 U.S.C. 154(b) by 0 days.

This patent is subject to a terminal disclaimer.

(21) Appl. No.: 09/732,840

(22) Filed: Dec. 8, 2000

(65) Prior Publication Data

US 2001/0039367 A1 Nov. 8, 2001

Related U.S. Application Data

(63) Continuation-in-part of application No. 09/659,895, filed on Sep. 12, 2000, and a continuation-in-part of application No. 09/660,162, filed on Sep. 12, 2000.
(60) Provisional application No. 60/178,877, filed on Jan. 28, 2000, provisional application No. 60/178,568, filed on Jan. 28, 2000, provisional application No. 60/169,632, filed on Dec. 8, 1999, and provisional application No. 60/169,561, filed on Dec. 8, 1999.

(51) Int. Cl.$^7$ .................... C07C 43/303; C07C 41/06
(52) U.S. Cl. .................... 568/591; 568/592; 568/593; 568/606; 568/608
(58) Field of Search ................ 568/591, 592, 568/593, 606, 608

(56) References Cited

U.S. PATENT DOCUMENTS

| | | |
|---|---|---|
| 3,082,172 A | 3/1963 | Temple et al. |
| 3,255,117 A | 6/1966 | Knapp et al. |
| 3,281,475 A | 10/1966 | Boettner et al. |
| 4,272,394 A | 6/1981 | Kaneko |
| 4,317,940 A | 3/1982 | Scardera et al. |
| 4,827,028 A | 5/1989 | Scardera et al. |
| 4,898,621 A | 2/1990 | Pruehs et al. |
| 4,902,834 A | 2/1990 | Otten et al. |
| 4,913,833 A | 4/1990 | Otten et al. |
| 4,925,587 A | 5/1990 | Schenker et al. |
| 5,073,286 A | 12/1991 | Otten et al. |
| 5,206,443 A | 4/1993 | Baur et al. |
| 5,294,365 A | 3/1994 | Welch et al. |
| 5,346,973 A | 9/1994 | Feustel et al. |
| 5,425,894 A | 6/1995 | Welch et al. |
| 5,576,281 A | 11/1996 | Bunch et al. |
| 5,677,273 A | 10/1997 | Schmid et al. |
| 5,921,910 A | 7/1999 | Schmid et al. |

FOREIGN PATENT DOCUMENTS

| | | |
|---|---|---|
| DE | 2252186 A | 5/1974 |
| DE | 2556544 A | 6/1977 |
| EP | 0337760 A | 10/1989 |
| EP | 0638635 A1 | 2/1995 |
| EP | 0675942 B1 | 7/1997 |
| GB | 2158080 A | 11/1985 |
| WO | WO 93/04153 A1 | 3/1993 |
| WO | WO 94/22800 A1 | 10/1994 |
| WO | WO 95/13260 A1 | 5/1995 |
| WO | WO 96/00253 A | 1/1996 |
| WO | WO 96/12001 A1 | 4/1996 |
| WO | WO 98/17379 A1 | 4/1998 |
| WO | WO 99/06466 A1 | 2/1999 |

*Primary Examiner*—Rosalynd Keys
(74) *Attorney, Agent, or Firm*—Kevin L Waugh; C. Brant Cook; Kim W. Zerby

(57) ABSTRACT

A process for preparing an ether-capped poly(oxyalkylated) alcohol surfactant is provided. The alcohol has the formula:

$$RO(R^1O)_xCH(CH_3)OR^2$$

wherein R is selected from the group consisting of linear or branched, saturated or unsaturated, substituted or unsubstituted, aliphatic or aromatic hydrocarbon radicals having from about 1 to about 30 carbon atoms; $R^1$ may be the same or different, and is independently selected from the group consisting of branched or linear $C_2$ to $C_7$ alkylene in any given molecule; x is a number from 1 to about 30; and $R^2$ is a six membered substituted or unsubstituted, saturated or unsaturated, cyclic or aromatic hydrocarbon radical.

17 Claims, No Drawings

PROCESS FOR PREPARING ETHER-CAPPED POLY(OXYALKYLATED) ALCOHOL SURFACTANTS

RELATED APPLICATIONS

This application claims priority to U.S. Provisional Application No. 60/169,632, filed on Dec. 8, 1999; U.S. Provisional Application No. 60/178,877, filed on Jan. 28, 2000; and is a continuation-in-part U.S. application Ser. No. 09/659,895, filed Sep. 12, 2000; U.S. Provisional Application No. 60/169,561, filed on Dec. 8, 1999; U.S. Provisional Application No. 60/178,568, filed Jan. 28, 2000; and is a continuation-in-part U.S. Application No. 09/660,162, filed Sep. 12, 2000.

TECHNICAL FIELD

The present invention relates to a process for preparing low-foaming nonionic surfactants and more particularly to a process for preparing ether-capped poly(oxyalkylated) alcohol surfactants which have superior spotting and filming benefits in dishwashing and hard surface cleaning applications, as well as suds suppression in detergent compositions.

BACKGROUND OF THE INVENTION

Due to the varied nature of different cleaning compositions, different surfactants are better suited for some applications while being less suited or totally unsuitable for other applications. Nonionic surfactants, such as alcohol ethoxylates and alkyl glucose amides, are of considerable importance in detergent products. Under some conditions, nonionic surfactants aid cleaning of greasy soils and inhibit the formation of calcium soap. However, conventional nonionic surfactants designed for effective cleaning in laundry products form liquid crystalline phases on mixing with water. These phases can hinder the rate of mixing with water and lead to undesirable optical properties of thin films on solution drying. For example, conventional nonionics sprayed on the surface of granules to achieve target density can give rise to poor granule dissolution and residue in horizontal axis machine dispensers. Conventional nonionics formulated at high levels in liquid products can lead to poor rates of mixing with water. Conventional nonionics in window and floor cleaners can form visible liquid crystalline films on drying that increase the effort required by the consumer to achieve good results. Similarly, a nonionic surfactant for use in an automatic dishwashing machine would need to minimize foam production and not leave undesirable spots and films on the cleaned surfaces.

On account of the foregoing technical constraints as well as consumer needs and demands, product compositions are undergoing continual change and improvement. Moreover, environmental factors such as the need for biodegradable materials, the restriction of phosphate, the desirability of providing ever-better cleaning results with less product, and the use of less thermal energy and less water to assist the washing process, have all driven the need for improved compositions.

Accordingly, the need remains for new surfactants that are suitable for use in a variety of compositions which can provide improve dissolution of solid products (like bars and tablets) and granular products, improved rates of mixing of liquid products with water, improved streaking and filming performance in hard surface cleaners and automatic dishwashing products, and good cleaning, suds control and biodegradability, while avoiding incompatibility with other cleaning surfactants and/or bleach.

SUMMARY OF THE INVENTION

In accordance with a first aspect of the present invention, a process for preparing an ether-capped poly(oxyalkylated) alcohol surfactant is provided. The surfactant has the formula:

$$RO(R^1O)_xCH(CH_3)OR^2$$

wherein R is selected from the group consisting of linear or branched, saturated or unsaturated, substituted or unsubstituted, aliphatic or aromatic hydrocarbon radicals having from about 1 to about 30 carbon atoms; $R^1$ may be the same or different, and is independently selected from the group consisting of branched or linear $C_2$ to $C_7$ alkylene in any given molecule; x is a number from 1 to about 30; and $R^2$ is a six membered substituted or unsubstituted, saturated or unsaturated, cyclic or aromatic hydrocarbon radical.

The process comprises the steps of:

(a) providing a vinyl ether of the formula $$R^2OCH=CH_2$$

wherein $R^2$ is as defined above;

(b) providing an alkoxylated alcohol of the formula $$RO(R^1O)_xH$$

wherein R, $R^1$, and x, are as defined above;

(c) reacting the vinyl ether with said alkoxylated alcohol in the presence of a catalytically effective amount of a catalyst to form the ether-capped poly(oxyalkylated) alcohol, wherein reaction of the vinyl ether with the alkoxylated alcohol is conducted as a temperature of from about 0° C. to about 60° C. and said catalyst is a sulfonic catalyst; and (d) quenching the reaction of step (c) by the addition of a base.

These and other aspects, features and advantages will become apparent to those of ordinary skill in the art from a reading of the following detailed description and the appended claims. All percentages, ratios and proportions herein are by weight, unless otherwise specified. All temperatures are in degrees Celsius (° C.) unless otherwise specified. All documents cited are in relevant part, incorporated herein by reference.

DETAILED DESCRIPTION OF THE INVENTION

Once again, the present invention is directed toward a process for producing a low-foaming nonionic surfactant for use in detergent and other cleaning compositions.

It has been surprisingly discovered in accordance with the present invention that significant improvements in spotting and filming characteristics and, when used in conjunction with high cloud point surfactants, in the removal of greasy soils relative to conventional surfactants, are provided via the ether-capped poly(oxyalkylene) alcohol surfactants of the present invention.

The novel surfactants of the present invention comprise ether-capped poly(oxyalkylated) alcohols having the formula:

$$RO(R^1O)_xCH(CH_3)OR^2.$$

In one aspect of the present invention R is a linear or branched, saturated or unsaturated, substituted or unsubstituted, aliphatic hydrocarbon radical having from about 1 to about 30 carbon atoms, preferably from about 1 to about 20 carbon atoms. Even more preferably, R is a linear or branched, saturated, aliphatic hydrocarbon radical having from about 4 to about 18, preferably from about 8 to about 16, carbon atoms.

In the present invention $R^2$ is a six membered substituted or unsubstituted, saturated or unsaturated, cyclic or aromatic hydrocarbon radical.

In another embodiment of this aspect of the present invention $R^2$ is selected from the group consisting of:

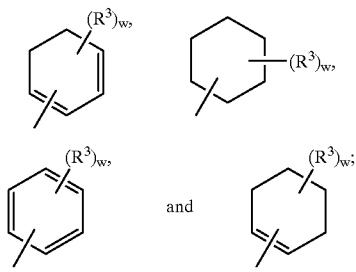

wherein each $R^3$ is independently selected from the group consisting of hydrogen and linear or branched, saturated or unsaturated, substituted or unsubstituted, aliphatic hydrocarbon or alkoxy radicals having from about 1 to about 10 carbon atoms; or each $R^3$ is a saturated or unsaturated, substituted or unsubstituted, alicyclic or aromatic hydrocarbon radical having from about 1 to about 10 carbon atoms, which is fused to the ring; and w is an integer from 1 to 3.

In another embodiment of this aspect of the present invention $R^2$ is selected from the group consisting of:

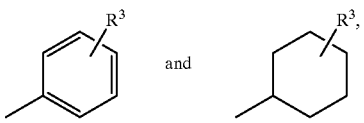

wherein each $R^3$ is defined as above.

In another embodiment of this aspect of the present invention $R^2$ is selected from the group consisting of:

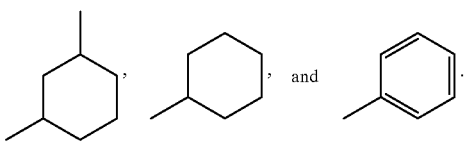

In one aspect of the present invention, when x is greater than 2, $R^1$ may be the same or different. That is, $R^1$ may vary between any of the $C_2$ to $C_7$ alkylene units as described above. For instance, if x is 3, $R^1$ may be selected to form ethyleneoxy(EO) or propyleneoxy(PO) and may vary in order of (EO)(PO)(EO), (EO)(EO)(PO); (EO)(EO)(EO); (PO)(EO)(PO); (PO)(PO)(EO) and (PO)(PO)(PO). Of course, the integer three is chosen for example only and the variation may be much larger with a higher integer value for x and include, for example, multiple (EO) units and a much smaller number of (PO) units. Similarly, ethylene, and propylene are chosen for example only and the variation may be much larger with selection of linear or branched butylene, pentylene, hexylene and/or heptylene. Preferably, x is from about 2 to about 20, and each $R^1$ is ethylene or propylene. More preferably, x is from about 4 to about 12, and each $R^1$ is ethylene.

The surfactants of the present invention can be prepared via the following process.

In one embodiment of this aspect of the present invention the step of reacting of vinyl ether with alkoxylated alcohol is conducted in the presence of a sulfonic catalyst. Suitable sulfonic catalysts include sulfonic acids and their salts such as p-toluenesulfonic acid, methanesulfonic acid, trifluoromethanesulfonic acid, 4-bromobenzene sulfonic acid, naphthalenesulfonic acid, (±)-10-camphorsulfonic acid, xylenesulfonic acid, cumenesulfonic acid, alkylbenzene sulfonic acids and mixtures thereof.

Preferred catalysts include methanesulfonic acid and p-toluenesulfonic acid.

Mixtures of catalysts are also within the scope of the present invention. Similarly, the uses of supported, such as in a column for a continuous reaction, and unsupported catalysts are also within the scope of the present invention.

The catalysts are preferably employed at amounts of about 0.005 mol % to about 20.0 mol %, more preferably from about 0.01 mol % to about 10.0 mol %, even more preferably from about 0.01 mol % to about 5.0 mol %, even more preferably still from about 0.01 mol % to about 1.5 mol %, based on the number of moles of alkoxylated alcohol in step (c) of the process.

In one embodiment of this aspect of the present invention the reaction is conducted in the presence of a solvent, or mixtures of solvents. It is preferred that the solvent be a polar aprotic solvent. Suitable solvents include, but are not limited to, hexane, benzene, toluene, xylene, mesitylene, dichloromethane, tetrahydrofuran, dioxane, chloroform, diethylether, methyl tert-butylether, acetone, acrylonitrile, or the like. Furthermore, the reaction is conducted at temperatures ranging from about 0° C. to about 60° C., and more preferably from about 10° C. to about 60° C. Lastly, the reaction is preferably conducted at pressures ranging from about 0.5 atmospheres to about 100 atmospheres, and more preferably from about 0.8 atmospheres to about 10 atmospheres.

In another embodiment of this aspect of the present invention the step of reacting vinyl ether with alkoxylated alcohol is conducted in the absence of a solvent.

Further disclosure on suitable solvents and catalysts can be found in "Advanced Organic Chemistry", by Jerry March, 4th ed., Wiley-Interscience, 1992, "Comprehensive Organic Transformations" by Richard C. Larock, VCH Publishers, 1989, and "Protective Groups in Organic Synthesis" 3RD ed. by Theodora W. Greene and Peter G. M. Wuts, Wiley-Interscience, 1999 the relevant portions of which are incorporated herein by reference.

In one embodiment of the present invention, the process is performed as a batch process. That is, the reaction is let to proceed to completion, or near completion, and then final product is removed. In another embodiment of the present invention, the process is performed as a continuous process. That is, the product of the process is continuously removed from the reaction vessel while starting material is added at a comparable rate.

In one embodiment of the present invention the vinyl ether is reacted with the alkoxylated alcohol at a mole ratio of from about 5:1 to about 0.5:1, more preferably from about 3:1 to about 0.75:1, more preferably still from about 1.5:1 to about 0.9:1.

In one embodiment of the process of the present invention the process may be conducted in an inert gas. This may be done by sparging with any suitable inert gas, such as nitrogen, helium, neon, or argon.

In the process of the present invention, step (d) is a step in which the reaction step (c) is quenched by the addition of base. The amount of the ether capped poly(oxyalkylated) alcohol surfactant present in the reaction mixture will depend upon many factors, including but not limited to, starting materials, temperature, catalyst selection and the like. Quenching stops the reaction of the starting materials, and ensures that any ether capped poly(oxyalkylated) alcohol surfactant produced does not undergo further reaction or revert back to the starting materials. The quenching of step (c) produces a mixture which contains ether capped poly (oxyalkylated) alcohol surfactant, as well as unreacted starting materials, catalyst and the products of any side reactions. In one embodiment of this present invention, the quenching of the reaction of step (c) is done when the reaction mixture preferably contains at least 90%, more preferably at least 95% by weight of ether capped poly(oxyalkylated) alcohol surfactant. The remaining portion of the mixture, up to 10%, more preferably up to 5% by weight, comprises unreacted starting material as well as products of side reactions, such as byproduct acetals. In one aspect of this embodiment of the present invention the base may be optionally selected from the group consisting of alkali metal carbonates, alkali metal bicarbonates, alkali metal hydroxides, alkali metal alcoholates, alkanolamines, alkylamines, aromatic amines and mixtures thereof. In a further aspect of the present invention the base may be optionally selected from the group consisting of potassium carbonate, sodium carbonate, sodium bicarbonate, sodium methoxylate, sodium ethoxylate, potassium tert-butyloxylate, triethylamine, triethanolamine and mixtures thereof. In another aspect of this embodiment of the present invention, the base may be in the form of an aqueous solution. In a further aspect of this embodiment of the present invention, the aqueous solution may be at a temperature of from about 20° C. to about 60° C.

The expression "product of step (c)" is meant to include not only the ether-capped poly(oxyalkylated) alcohol surfactant but also any unreacted starting materials or any materials produced from side reactions which would be present at the conclusion of step (c).

In one embodiment of the present invention the process of the present invention may optionally further comprise a step (e). Step (e) is removal of color bodies and/or odors from the product of step (c). In one aspect of this embodiment of the present invention removal of the color bodies and/or odors is obtained by contacting the product of step (c) with a reagent. The reagent can either be an oxidant, or a reductant. Suitable oxidants include hydrogen peroxide. Suitable reductants include sodium borohydride, and hydrogen over a palladium/carbon catalyst. In a further aspect of this embodiment of the present invention the color bodies and/or odors are removed by contacting the product of step (c) first with an oxidant and then a reductant, or first with a reductant and then an oxidant. The color bodies may also be removed by treating the product mixture with activated charcoal (carbon).

In one embodiment of the present invention the ether-capped poly(oxyalkylated) alcohol surfactant produced in steps (c) or (d) may optionally be removed from the product of steps (c) or (d) by centrifuging.

A representative example of this synthetic route of this aspect of the invention is demonstrated via the following diagram.

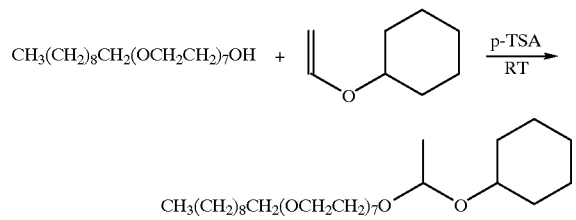

The ether-capped poly(oxyalkylated) alcohol surfactant product is then collected by means common in the art such as extraction. If desired, the surfactant may be further treated by stripping, distillation or various other means before use. The surfactant made by the process disclosed herein may contain related impurities, which will not adversely affect performance.

The following examples are illustrative of the present invention, but are not meant to limit or otherwise define its scope. All parts, percentages and ratios used herein are expressed as percent by weight unless otherwise specified.

EXAMPLES

Example 1

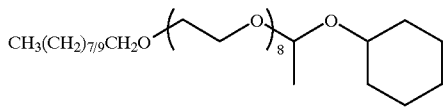

Preparation of $C_{9/11}H_{19/23}EO_8$-cyclohexyl acetal

Neodol 91-8 (20.00 g, 39.1 mmol) is placed into a 250 ml three-necked round-bottomed flask, fitted with a heating mantle, magnetic stirrer, internal thermometer and argon inlet and dried under vacuum at 75° C. After cooling to ambient, cyclohexyl vinyl ether (5.04 g, 39.9 mmol) is added. p-Toluenesulfonic acid monohydrate (0.112 g, 0.59 mmol) is added to the mixture and stirred to dissolve. An exotherm is observed starting from 22° C. and ending at 30° C., with the development of a precipitate. After 16 minutes of reaction time, the reaction is adjusted to pH ≧7 with triethanolamine, filtered and then stripped in a Kugelrohr oven (50° C., 0.1 mm Hg) to yield a quantitative amount of a near colorless liquid.

Example 2

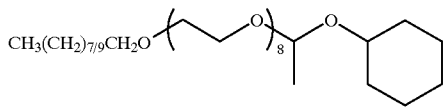

Preparation of $C_{9/11}H_{19/23}EO_8$-cyclohexyl acetal

Neodol 91-8 (900.0 g, 1.76 mol) is placed into a 3 L three-necked rounded bottomed flask, fitted with a heating mantel, mechanical stirrer, internal thermometer, and vacuum/argon take-off adapter. The contents are dried under vacuum at 80° C. for 30 min. A portion of the dry Neodol 91-8 (20 g) is set aside after the contents are cooled to room temperature. Cyclohexylvinyl ether (217.82 g, 1.73 mol) is then added to the reaction mixture. The reagents are cooled to about 10° C. at which point methanesulfonic acid (1.80 mL) and the 20 g portion of Neodol set aside are combined and added to the reaction mixture via syringe, subsurface, in one portion. The reaction mixture exotherms with ice bath control to 22° C. After 1 hour, the mixture is quenched with 15% sodium carbonate solution (35 mL). The mixture is placed under vacuum by stripping in a Kugelrohr oven (25° C., 0.1 mm Hg) for 10 min. The product is filtered to yield a quantitative amount of a near colorless liquid.

Example 3

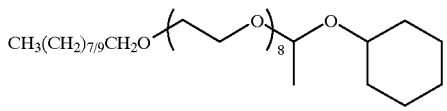

Preparation of $C_{9/11}H_{19/23}EO_8$-cyclohexyl acetal

Neodol 91-8 (100.0 g, 195.7 mmol) is placed into a 250 ml three-necked rounded bottomed flask, fitted with a heating mantel, magnetic stirrer, internal thermometer, and vacuum/argon take-off adapter. The contents are dried under vacuum at 80° C. for 10 min. After cooling to ambient, methanesulfonic acid (0.28 g, 2.9 mmol) is added. Cyclohexylvinyl ether (25.19 g, 199.6 mmol) is then added dropwise to the reaction mixture over 30 minutes with an observed exotherm to about 40° C. Five minutes after the completion of the addition of the cyclohexyl vinyl ether, the reaction is adjusted to pH $\geq 7$ with triethanolamine, filtered and then stripped in a Kugelrohr oven (50° C., 0.1 mm Hg) to yield a quantitative amount of a near colorless liquid.

Example 4

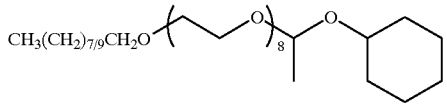

Preparation of $C_{9/11}H_{19/23}EO_8$-cyclohexyl acetal

Anhydrous Neodol 91-8 (18.21 g, 35.6 mmol) is blended with cyclohexyl vinyl ether (12.10 g, 95.9 mmol) and placed into a 30 ml gas tight syringe. Methanesulfonic acid (0.14 g, 1.5 mmol) is blended with anhydrous Neodol 91-8 (31.79 g, 62.2 mmol) and placed into a 30 ml gas tight syringe. The syringes are loaded into a syringe pump. The contents of the syringes (at ambient) are added simultaneously at an equal rate to a 250 ml three-necked round-bottomed flask, equipped with a magnetic stirrer, internal thermometer and argon inlet. Total addition time is 60 minutes and an exotherm to 30° C. is observed. Thirty minutes after the addition is complete, the reaction pH is adjusted to $\geq 7$ with 15% sodium carbonate. The mixture is placed under vacuum by stripping in a Kugelrohr oven (50° C., 0.1 mm Hg) for 10 min. The product is filtered to yield a quantitative amount of a near colorless liquid.

Example 5

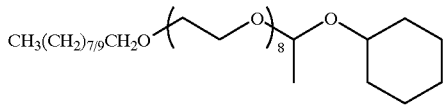

Preparation of $C_{9/11}H_{19/23}EO_8$-cyclohexyl acetal

Cyclohexyl vinyl ether (13.0 g, 103.0 mmol) is placed into a 250 ml three-necked round-bottomed flask, fitted with a magnetic stirrer, internal thermometer and argon inlet. Methanesulfonic acid (0.14 g, 1.5 mmol) is blended with anhydrous Neodol 91-8 (50.9 g, 99.6 mmol) and placed into a 30 ml syringe. The syringe is placed into a syringe pump and the contents are added to the reaction flask over 3 hours. An exotherm to 25° C. is observed. Thirty minutes after the addition is complete, the reaction pH is adjusted to $\geq 7$ with 15% sodium carbonate. The mixture is placed under vacuum by stripping in a Kugelrohr oven (50° C., 0.1 mm Hg) for 10 min. The product is filtered to yield a quantitative amount of a yellow liquid.

Example 6

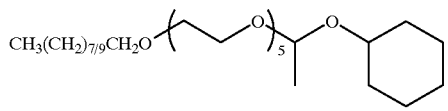

Preparation of $C_{9/11}H_{19/23}EO_5$-cyclohexyl acetal

Neodol 91-5 (100.0 g, 263.9 mmol) is placed into a 250 ml three-necked round-bottomed flask, fitted with a heating mantel, magnetic stirrer, internal thermometer, and vacuum/argon take-off adapter. The contents are dried under vacuum at 80° C. for 10 min. A portion of the dry Neodol 91-5 (2 g) is set aside after the contents are cooled to room temperature. Cyclohexyl vinyl ether (32.97 g, 261.2 mmol) is then added to the reaction mixture. The reagents are cooled to about 15° C. at which point methanesulfonic acid (0.28 g, 2.9 mmol) and the 2 g portion of Neodol set aside are combined and added to the reaction mixture via syringe, subsurface and in one portion. The reaction mixture exotherms to 40° C. After 5 minutes, the reaction pH is adjusted to $\geq 7$ with 15% sodium carbonate. The mixture is placed under vacuum by stripping in a Kugelrohr oven (50° C., 0.1 mm Hg) for 10 min. The product is filtered to yield a quantitative amount of a near colorless liquid.

The ether-capped poly(oxyalkylated) alcohol surfactants produced by the process of the present invention may be used in a variety of applications, such as wetting agents, antifoaming agents, in drilling muds, etc., in a wide range of fields, such as in biocides, meat cleaning, foods, pharmaceuticals, polymer latexes, etc. As noted previously, they may also be used in cleaning compositions, such as automatic dishwashing detergent compositions, light duty liquid, hand dishwashing compositions, hard surface cleaning compositions, laundry compositions, such as granular or liquid laundry detergents, or in personal cleansing compositions, such as shampoos, body bars, and body washes. The ether-capped poly(oxyalkylated) alcohol surfactants have properties of good biodegradability, low-sudsing as well as cleaning which allows them to be used in a wide range of diverse and radically different applications. For any particular application which desires a specific physical property, such as HLB or cloud point, an ether-capped poly(oxyalkylated) alcohol surfactant, or mixtures of ether-capped poly(oxyalkylated) alcohol surfactant, may be used. The desired propertied are obtained varying the selection of R, $R^1$, x and $R^2$ for any ether-capped poly(oxyalkylated) alcohol surfactant or mixtures of these surfactants. Further examples of possible application for these surfactants can be found in "Nonionic Surfactants" edited by Martin J. Schinck, Surfactant Science Series, Marcel Dekker, NY, Volume 1; "Nonionic Surfactants: Physical Chemistry" edited by Martin J. Schinck, Surfactant Science Series, Marcel Dekker, NY, Volume 23; "Nonionic Surfactants: Polyoxyalkylene Block Copolymers" edited by Vaughn M. Nace, Surfactant Science Series, Marcel Dekker, NY, Volume 60; and L. G. Lundsted and I. R. Schmolka, in "Block and Graft Copolymerization", Vol. 2 (R. J. Ceresa, ed.), John Wiley & Sons, Ltd., London, 1976, pp.113–272, incorporated herein by reference.

What is claimed is:

1. A process for preparing an ether-capped poly(oxyalkylated) alcohol having the formula:

wherein R is selected from the group consisting of linear or branched, saturated or unsaturated, substituted or unsubstituted, aliphatic or aromatic hydrocarbon radicals having from about 1 to about 30 carbon atoms; $R^1$ may be the same or different, and is independently selected from the group consisting of branched or linear $C_2$ to $C_7$ alkylene in any given molecule; x is a number from 1 to about 30; and $R^2$ is a six membered substituted or unsubstituted, saturated or unsaturated, cyclic or aromatic hydrocarbon radical;

comprising the steps of:

(a) providing a vinyl ether of the formula

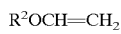

wherein $R^2$ is as defined above;

(b) providing an alkoxylated alcohol of the formula

wherein R, $R^1$, and x, are as defined above;

(c) reacting the vinyl ether with said alkoxylated alcohol in the presence of a catalytically effective amount of a catalyst to form the ether-capped poly(oxyalkylated) alcohol, wherein reaction of the vinyl ether with the alkoxylated alcohol is conducted as a temperature of from about 0° C. to about 60° C. and said catalyst is a sulfonic catalyst; and (d) quenching the reaction of step (c) by the addition of a base.

2. The process as claimed in claim 1 wherein R is a linear or branched, saturated or unsaturated, substituted or unsubstituted, aliphatic hydrocarbon radical having from about 1 to about 20 carbon atoms.

3. The process as claimed in claim 2 wherein R is a linear or branched, saturated, aliphatic hydrocarbon radical having from about 4 to about 18 carbon atoms.

4. The process as claimed in claim 1 wherein about 0.005 mol % to about 20.0 mol % of said catalyst is used in said step (c).

5. The process as claimed in claim 1 wherein said sulfonic catalyst is selected from the group consisting of methanesulfonic acid, p-toluenesulfonic acid and mixtures thereof.

6. The process as claimed in claim 5 wherein about 0.01 mol % to about 1.5 mol % of said catalyst is used in step (c).

7. The process as claimed in claim 1 wherein said step of reacting the vinyl ether with the alkoxylated alcohol is conducted in the presence of a solvent.

8. The process as claimed in claim 6 wherein said solvent is selected from the group consisting of hexane, benzene, toluene, xylene, mesitylene, dichloromethane, tetrahydrofuran, dioxane, chloroform, diethylether, methyl tert-butylether, acetone, acetonitrile, and mixtures thereof.

9. The process as claimed in claim 1 wherein said step of reacting the vinyl ether with the alkoxylated alcohol is conducted in the absence of a solvent.

10. The process as claimed in claim 1 wherein $R^2$ is selected from the group consisting of:

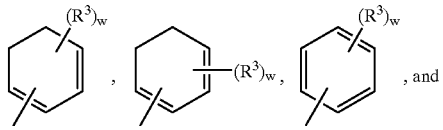

wherein each $R^3$ is independently selected from the group consisting of hydrogen and linear or branched, saturated or unsaturated, substituted or unsubstituted, aliphatic hydrocarbon or alkoxy radicals having from about 1 to about 10 carbon atoms, or each $R^3$ is a saturated or unsaturated, substituted or unsubstituted, alicyclic or aromatic hydrocarbon radical having from about 1 to about 10 carbon atoms, which is fused to the ring; and w is an integer from 1 to 3.

11. The process as claimed in claim 1 wherein $R^2$ is selected from the group consisting of:

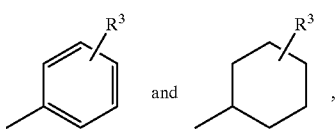

wherein each $R^3$ is independently selected from the group consisting of hydrogen, linear or branched, saturated or unsaturated, substituted or unsubstituted, aliphatic hydrocarbon or alkoxy radicals having from about 1 to about 10 carbon atoms, or each $R^3$ is a saturated or unsaturated, substituted or unsubstituted, alicyclic or aromatic hydrocarbon radical having from about 1 to about 10 carbon atoms, which is fused to the ring; and w is an integer from 1 to 3.

12. The process as claimed in claim 1 wherein $R^2$ is selected from the group consisting of:

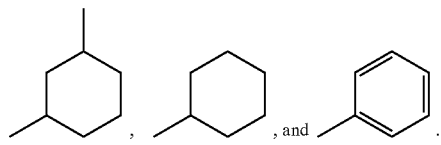

13. The process as claimed in claim 12 wherein R is a linear or branched, saturated, alphatic hydrocarbon radical having from about 4 to about 18 carbon atoms.

14. The process as claimed in claim 1 wherein said base is selected from the group consisting of alkali metal carbonates, alkali metal bicarbonates, alkali metal hydroxides, alkali metal alcoholates, alkanolamines, alkyl amines, aromatic amines, and mixtures thereof.

15. The process as claimed in claim 14 wherein said base is selected from the group consisting of potassium carbonate, sodium carbonate, sodium bicarbonate, sodium methoxylate, sodium ethoxylate, potassium tert-butyloxylate, triethylamine, triethanolamine and mixtures thereof.

16. The process as claimed in claim 1 wherein said process further comprises step (e) removing of color bodies and odors from the product of step (c).

17. The process as claimed in claim 1 wherein the mixture produced by step (d) comprises at least 90% by weight of said ether-capped poly(oxyalkylated) alcohol.

* * * * *